(12) United States Patent
Wood et al.

(10) Patent No.: US 8,129,548 B2
(45) Date of Patent: Mar. 6, 2012

(54) PROCESS FOR THE PURIFICATION OF 1,4-BUTANEDIOL

(75) Inventors: Michael Anthony Wood, London (GB); Robert Wild, London (GB); Simon Wayne Jackson, London (GB)

(73) Assignee: Davy Process Technology Limited, London (GB)

( * ) Notice: Subject to any disclaimer, the term of this patent is extended or adjusted under 35 U.S.C. 154(b) by 442 days.

(21) Appl. No.: 11/575,206

(22) PCT Filed: Sep. 29, 2005

(86) PCT No.: PCT/GB2005/003741
§ 371 (c)(1),
(2), (4) Date: Jul. 20, 2007

(87) PCT Pub. No.: WO2006/037957
PCT Pub. Date: Apr. 13, 2006

(65) Prior Publication Data
US 2007/0260073 A1    Nov. 8, 2007

(30) Foreign Application Priority Data

Oct. 1, 2004 (GB) .................................. 0421928.3

(51) Int. Cl.
*C07D 307/00* (2006.01)
*C07D 307/02* (2006.01)
*C07C 27/04* (2006.01)

(52) U.S. Cl. .......................... 549/429; 549/475; 568/864

(58) Field of Classification Search .................. 549/475, 549/479, 508, 509, 429; 568/864
See application file for complete search history.

(56) References Cited

U.S. PATENT DOCUMENTS

| 4,584,419 A | 4/1986 | Sharif et al. |
| 4,751,334 A | 6/1988 | Turner et al. |
| 4,795,824 A | 1/1989 | Kippax et al. |
| 5,008,408 A | 4/1991 | Fischer et al. |
| 6,204,395 B1 * | 3/2001 | Tuck et al. ..................... 549/325 |
| 6,387,224 B1 | 5/2002 | Pinkos et al. |
| 6,844,452 B2 * | 1/2005 | Wood et al. ................... 549/475 |
| 2003/0100777 A1 | 5/2003 | Wood et al. |

FOREIGN PATENT DOCUMENTS

| DE | 19801089 | 7/1998 |
| EP | 0601571 A1 | 6/1994 |
| EP | 0885864 A1 | 12/1998 |
| EP | 0912488 B1 | 5/1999 |
| EP | 0922022 B1 | 6/1999 |
| EP | 1220822 B1 | 7/2002 |
| EP | 1237833 B1 | 9/2002 |
| EP | 1428812 A1 | 6/2004 |
| GB | 0329152 | 5/1930 |
| JP | 2003026622 | 1/2003 |
| WO | 88/00937 A1 | 2/1988 |
| WO | 90/08127 A1 | 7/1990 |
| WO | 97/36846 A1 | 10/1997 |
| WO | 97/43234 A1 | 11/1997 |
| WO | 97/43242 A1 | 11/1997 |
| WO | 99/25675 A1 | 5/1999 |
| WO | 99/25678 A1 | 5/1999 |
| WO | 99/48852 A1 | 9/1999 |
| WO | 01/27058 A1 | 4/2001 |
| WO | 01/44148 A1 | 6/2001 |
| WO | 03/006446 A1 | 1/2003 |
| WO | 2005/051875 A1 | 6/2005 |
| WO | 2005/051885 A1 | 6/2005 |

OTHER PUBLICATIONS

International Search Report and Written Opinion from PCT/GB2005/003741, dated Dec. 1, 2005.
Written Opinion from PCT/GB2005/003741, dated Apr. 12, 2007.

* cited by examiner

*Primary Examiner* — Taylor Victor Oh
(74) *Attorney, Agent, or Firm* — Senniger Powers LLP

(57) ABSTRACT

A process for the purification of a crude liquid feed stream comprising 1,4-butanediol and a minor amount of 2-(4-hydroxybutoxy)-tetrahydrofuran and/or precursors thereof wherein the process comprises passing the crude feed in the presence of hydrogen in a reaction zone over a heterogeneous liquid tolerant copper catalyst in the liquid phase at hydrogenation conditions and recovering a purified stream of 1,4-butanediol having a lower amount of 2-(4-hydroxybutoxy)-tetrahydrofuran than the crude liquid feed stream.

14 Claims, No Drawings

PROCESS FOR THE PURIFICATION OF 1,4-BUTANEDIOL

CROSS-REFERENCE TO RELATED APPLICATIONS

This application is based on and claims the benefit of International (PCT) Application Serial No. PCT/GB2005/003741, filed Sep. 29, 2005, which claims priority from GB 0421928.3, filed Oct. 1, 2004, both of which are herein incorporated by reference in their entirety.

The present invention relates to the production of 1,4-butanediol. More particularly it relates to a process for the production of 1,4-butanediol in which the presence of the by-products 2-(4-hydroxybutoxy)-tetrahydrofuran and its precursors are reduced such that purification of the 1,4-butanediol by conventional distillation processes may be carried out.

Whilst several synthetic routes to 1,4-butanediol are known, one process for the production of 1,4-butanediol uses maleic anhydride as a starting material. This is esterified with an alkanol, usually a $C_1$ to $C_4$ alkanol such as methanol or ethanol, to yield the corresponding dialkyl maleate which is then subjected to hydrogenolysis to yield 1,4-butanediol and the alkanol which may be recycled to produce further dialkyl maleate. Processes and plant for the production of dialkyl maleates from maleic anhydride are described in, for example, U.S. Pat. No. 4,795,824 and WO90/08127 which are incorporated by reference. The hydrogenolysis of diallyl maleates to yield 1,4-butanediol is discussed further in, for example U.S. Pat. No. 4,584,419, U.S. Pat. No. 4,751,334 and WO88/00937 the disclosures of which are incorporated by reference.

The hydrogenolysis of the diallyl maleate, such as dimethyl maleate or diethyl maleate, may also lead to the production of amounts of the valuable co-products, γ-butyrolactone and tetrahydrofuran. Since there is a ready market for these by-products, their co-production with 1,4-butanediol may not be disadvantageous.

One other by-product that is formed is the cyclic acetal 2-(4-hydroxybutoxy)-tetrahydrofuran which has the formula:

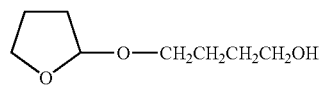

Without wishing to be bound by any theory, and while there have been various suggestions, it is now believed that this by-product is formed by reaction of the 1,4-butanediol with 2-hydroxytetrahydrofuran which is a potential intermediate in the sequence of the hydrogenolysis reactions and/or it may be formed by the dehydrogenation of the 1,4-butanediol to hydroxybutyroaldehyde and cyclisation thereof to the more stable 2-hydroxytetrahydrofuran. The mechanisms for formation of all these products and co-products have not been fully elucidated. However, their production is consistent with the following reaction scheme:

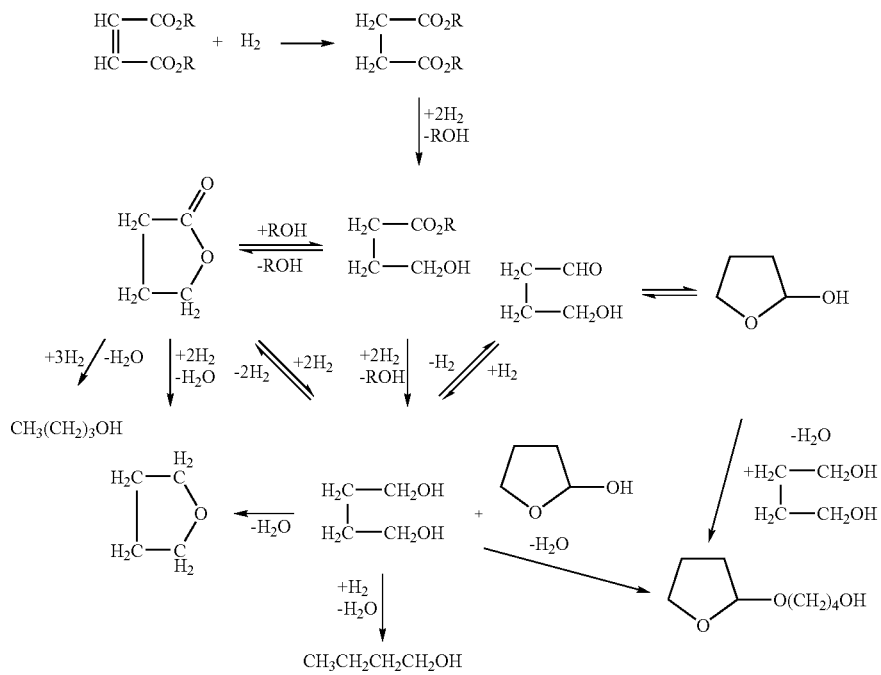

The presence of the 2-(4-hydroxybutoxy)-tetrahydrofuran is particularly disadvantageous since its boiling point lies very close to that of 1,4-butanediol and thus separation of this by-product from the desired product is difficult via conventional distillation since an azeotrope will be formed. It is therefore difficult, if not impossible, to produce a 1,4-butanediol product which is essentially free from the cyclic acetal and 1,4-butanediol produced by the hydrogenolysis route typically contains from about 0.15% by weight to about 0.20% by weight of the 2-(4-hydroxybutoxy)-tetrahydrofuran. Further, since 2-(4-hydroxybutoxy)-tetrahydrofuran may be produced by oxidation of the diol and oxidation may occur under the conditions at which distillation is conventionally carried out, the distillation process itself may actually result in an increase in the amount of 2-(4-hydroxybutoxy)- tetrahydrofuran present in the final product. Where distillation is used for the separation, complex systems such as divided wall distillation columns may be required.

The presence of even minor traces of 2-(4-hydroxybutoxy)-tetrahydrofuran in 1,4-butanediol is disadvantageous because it is a colour forming material in downstream applications.

Various proposals have been made to address the problem associated with the formation of 2-(4-hydroxybutoxy)-tetrahydrofuran. These proposals either concentrate on systems which enable the 2-(4-hydroxybutoxy)-tetrahydrofuran to be separated from the 1,4-butanediol or they relate to production processes for 1,4-butanediol in which for the amount of 2-(4-hydroxybutoxy)-tetrahydrofuran formed is limited.

U.S. Pat. No. 6,387,224 describes a process for separating by distillation a mixture of 1,4-butanediol and at least one 4-hydroxybutyraldehyde, its cyclic hemiacetal and its cyclic full acetals and at least one further alcohol. In the process, the distillation is carried out in the presence of an alkaline compound such as ammonia, an amine, an alkali metal compound or an alkaline earth metal compound. Whilst this process goes some way to addressing the problems of the prior art, it would be expensive to operate on a commercial scale due to the impact that the alkaline compounds would have on the materials required for the construction of the plant.

JP2003-026622 describes a method of purifying crude 1,4-butanediol which has been produced from butadiene. The crude product is hydrolysed, distilled to recover the fraction which contains 1,4-diacetoxybutene, the recovered fraction is then hydrogenated over a supported noble metal catalyst to reduce the presence of the unwanted compounds. The hydrogenated product is then hydrolysed. This process has high cost implications in view of the number of process steps required and the use of the noble metal catalyst.

EP0885864 describes a process in which the 1,4-butanediol is purified by melt crystallisation in order to avoid the distillation step which may lead to the production of additional 2-(4-hydroxybutoxy)-tetrahydrofuran.

WO97/36846 also describes a process for the purification of a 1,4-butanediol feed containing a minor amount of the 2-(4-hydroxybutoxy)-tetrahydrofuran. In this process, the cyclic acetal compound and its precursors are removed by adding water to an essentially pure 1,4-butanediol stream, the stream is then hydrogenated in the liquid phase over a nickel catalyst to reduce the level of 2-(4-hydroxybutoxy)-tetrahydrofuran, and the water and the final heavy impurities are removed by conventional distillation. Whilst this process offers certain advantages, it can only be performed on a 1,4-butanediol stream which has been obtained after an extensive distillation process and is not suitable for use on a crude reaction stream.

Whilst these processes go some way to addressing the problems associated with the presence of 2-(4-hydroxybutoxy)-tetrahydrofuran and its precursors in a product stream of 1,4-butanediol from maleic anhydride they still suffer from certain disadvantages and drawbacks. It is therefore desirable to provide a process which will enable the problems associated with the presence of 2-(4-hydroxybutoxy)-tetrahydrofuran and its precursors to be obviated in an efficient and cost-effective means.

It has now been found that the aforementioned problems can be solved by passing the crude liquid hydrogenation product stream from the vapour phase hydrogenation of dialkyl maleates, without further purification, over a heterogeneous copper based catalyst under appropriate temperatures and pressures in the liquid phase.

Thus according to the present invention there is provided a process for the purification of a crude liquid feed stream comprising 1,4-butanediol and a minor amount of 2-(4-hydroxybutoxy)-tetrahydrofuran and/or precursors thereof wherein the process comprises passing the crude feed in the presence of hydrogen in a reaction zone over a heterogeneous liquid tolerant copper catalyst in the liquid phase at hydrogenation conditions and recovering a purified stream of 1,4-butanediol having a lower amount of 2-(4-hydroxybutoxy)-tetrahydrofuran than the crude liquid feed stream.

By this means the presence of the 2-(4-hydroxybutoxy)-tetrahydrofuran and its precursors in the stream are reduced. The amount of 2-(4-hydroxybutoxy)-tetrahydrofuran and its precursors will typically be reduced by about 50 to 70% as determined by a developed Peak Acetal Test which is detailed below. The purified stream from the hydrogenation reaction zone may then be subjected to purification to provide 1,4-butanediol of high purity. Generally the 1,4-butanediol can be purified by conventional distillation processes to provide the high purity required for polymer grade 1,4-butanediol.

The "crude" liquid feed of the present invention will preferably be a liquid hydrogenation product stream from the vapour hydrogenation of dialkyl maleates which has not been subjected to prior purification.

The liquid phase hydrogenation may be carried out at any suitable conditions. However moderate pressures and low temperatures will generally be preferred. For example, the liquid feed stream may be subjected to a hydrogen pressure in the range of from about 5 barg to about 150 barg, more preferably from about 35 barg to about 100 barg. The temperature of the reaction zone will generally be in the range of from about 20° C. to about 150° C., more preferably from about 50° C. to about 130° C. The liquid hourly space velocity is generally in the range of from about 0.1 to about 10, more preferably from about 0.2 to about 5.

The hydrogen may be present in the crude feed in the form of dissolved hydrogen in the liquid stream and/or additional hydrogen may be added. Where additional hydrogen is added it will generally be provided to the reaction zone at a flow rate of about 1 to about 50 normal litres per hour, more preferably about 5 and about 30 normal litres per hour, per 0.05 litres of crude feed.

It will be acknowledged that it is surprising that at these modest conditions removal of the aldehyde and other precursors is so effective.

Any suitable copper based liquid tolerant heterogeneous catalyst may be used. A typical catalyst will be a copper chromite catalyst such as that available from Davy Process Technology, 20 Eastbourne Terrace, London under the designation PG 85/1. Other suitable catalysts include copper alumina, copper zinc or copper silica based catalysts.

The catalyst may be used with a promoter. Any suitable promoter may be used. Suitable promoters include manganese and barium.

The hydrogen may be stripped from the purified stream by conventional means.

The feed stream may be from any suitable source and may be a product stream from, for example, U.S. Pat. No. 6,100,410, U.S. Pat. No. 6,620,949, U.S. Pat. No. 7,498,450, U.S. Pat. No. 6,844,452, U.S. Pat. No. 7,598,404, U.S. Pat. No. 6,936,727, U.S. Pat. App. Pub. US 2007/0129565, U.S. Pat. No. 6,274,743, U.S. Pat. No. 6,204,395, U.S. Pat. No. 6,239,292, U.S. Pat. No. 4,584,419, U.S. Pat. No. 4,751,334 and U.S. Pat. No. 6,077,964 which are each incorporated herein by reference.

According to a further aspect of the present invention there is provided a process for the production of at least one $C_4$ compound selected from 1,4-butanediol, tetrahydrofuran and γ-butyrolactone comprising:

(a) contacting a solution of a di-($C_1$-$C_4$ alkyl) maleate with hydrogen in a hydrogenation zone under ester hydrogenation conditions in the presence of a heterogeneous ester hydrogenation catalyst to convert the di-($C_1$-$C_4$ alkyl) maleate to the at least one $C_4$ compound and a minor amount of 2-(4-hydroxybutoxy)-tetrahydrofuran;

(b) recovering from the hydrogenation zone a product stream containing the at least one $C_4$ compound and a minor amount of 2-(4-hydroxybutoxy)-tetrahydrofuran as a crude feed stream; and (c) without prior purification subjecting the crude feed stream to the purification process of the first aspect of the present invention.

The present invention will now be described, by way of example, with reference to the accompanying examples.

The minor amount of 2-(4-hydroxybutoxy)-tetrahydrofuran and its precursors in at least one $C_4$ compound is measured using the Peak Acetal Test. This Test involves the removal of lights from the 1,4-butanediol crude hydrogenation product at 120° C. and then further heating at 160° C. for three hours. The heating which is carried out using an isomantle heater, round bottom flask, condenser and collection pot is carried out tinder a blanket of nitrogen at atmospheric pressure. The procedure allows for the reaction of the precursors of the acetal and therefore reports the maximum acetal content possible in the product 1,4-butandiol stream if the crude hydrogenation product was subjected to purification by a standard distillation system. The residue is then analysed by gas chromatography.

EXAMPLE 1

A crude product stream from a production of 1,4-butanediol carried out in accordance with WO97/43242 was treated according to the process of the present invention at a reaction temperature of 60° C. and a pressure of 600 psig, a gas rate of 100 nlph and a LHSV of 1 $hr^{-1}$ over the catalyst PG85/1. The peak acetal content of the crude feed as measured by the Peal, Acetal Test was 0.429 wt % and that of the product was found to be 0.234 wt %, indicating a 50% removal.

EXAMPLE 2

The reaction of Example 1 was repeated at a temperature of 70° C. The peak acetal content of the crude feed as measured by the Peak Acetal Test was 0.429 wt % and that of the product was found to be 0.212 wt %.

EXAMPLE 3

The reaction of Example 1 was repeated at gas rate of 25 nlph. The peak acetal content of the crude feed as measured by the Peak Acetal Test was 0.429 wt % and that of the product was found to be 0.252 wt %.

EXAMPLES 4 TO 11

A 50 ml bed of copper chromite catalyst PG85/1 was activated by the following procedure. The gas rate was set to give the required gas velocity in the reactor and the pressure was set to 50 psig. The gas flow was established using $N_2$ and while the reactor was at room temperature the following procedure was commenced: the $H_2$ concentration was increased to 0.1% and the inlet temperature was brought up to 120° C. over 3 hours; the $H_2$ was monitored at the inlet and outlet above 100° C. and the $H_2$ inlet was kept at 0.1%; during the following steps it was ensured that the exotherm did not exceed 10° C. by reducing the $H_2$ inlet composition if necessary and the conditions were held until the exotherm reduced; the temperature was then increased by 10° C. until it reached 160° C.; when at 160° C. the $H_2$ in the exit gas only differed slightly from the inlet composition; after being held for 1 hour the inlet gas $H_2$ composition was increased to 0.2% over 1 hour and held for 2 hours; the $H_2$ in the inlet was then increased to 0.3% for 1 hour and held for 2 hours; the 12 in the inlet was then increased to 0.4% for 1 hour and held for 2 hours; the $H_2$ in the inlet was then increased to 0.5% and held until the $H_2$ at the inlet equalled the $H_2$ at the exit; the 0.5% $H_2$ in the inlet was then maintained and the temperature increased to 170° C. over 1 hour and it was ensured that the exotherm did not exceed 10° C. and held until $H_2$ at the inlet equalled the $H_2$ at the exit; the temperature was then maintained at 170° C.; the $H_2$ content at the inlet was then slowly increased to 1% over a minimum time of 1 hour and maintained until H, at the inlet equalled the $H_2$ at the exit; the exotherm was then monitored to keep it below 10° C., by reducing $H_2$ concentration if needed, then the $H_2$ concentration was increased up to 5% at 1% per hour; the $H_2$ at the inlet was increased slowly to 10% and maintained until $H_2$ at the inlet equalled the $H_2$ at the exit; the exotherm was monitored to keep it below 10° C.; the $H_2$ at the inlet was increased to 100% while malting sure the exotherm did not exceed 10° C.; the operating pressure was then increased and left under H, for 4 hours before the liquid feed was turned on.

A crude hydrogenation product containing 0.48 wt % of 2-(4-hydroxybutoxy)-tetrahydrofuran precursors was passed over the heated reaction zone under the conditions set out in Table 1.

TABLE 1

| Example | Feed LHSV $hr^{-1}$ | Temp ° C. | Pressure barg | $H_2$ flow NLPH | Product Acetal Precursor level wt % |
|---|---|---|---|---|---|
| 4 | 0.5 | 125 | 41.4 | 10 | 0.13 |
| 5 | 1.0 | 125 | 41.4 | 10 | 0.13 |
| 6 | 1.5 | 125 | 41.4 | 10 | 0.13 |
| 7 | 1.0 | 100 | 41.4 | 10 | 0.14 |
| 8 | 1.0 | 150 | 41.4 | 10 | 0.12 |
| 9 | 1.0 | 125 | 20.7 | 10 | 0.16 |
| 10 | 1.0 | 125 | 41.4 | 20 | 0.12 |
| 11 | 1.0 | 100 | 41.4 | 10 | 0.13 |

EXAMPLE 12

A further example demonstrated the present invention on a miniplant scale. A 250 ml bed of copper chromite catalyst PG85/1 was activated by the method described above. The reaction conditions are set out in Table 2.

TABLE 2

| Example | Feed LHSV hr$^{-1}$ | Temp °C. | Pressure barg | H$_2$ flow NLPH | Product Acetal Precursor level wt % |
|---|---|---|---|---|---|
| 12 | 0.125 | 120 | 41.4 | 25 | 0.19 |

The crude hydrogenation product had a Peak Acetal of 0.46 wt % following treatment this resulted in a level of 19%. The material from this miniplant was distilled via the conventional distillation processes to provide 1,4-butanediol product that contained 0.8% 2-(4-hydroxybutoxy)-tetrahydrofuran. This demonstrated that a high purity polymer grade 1,4-butanediol can be achieved in high yield.

The invention claimed is:

1. A process for the purification of a crude liquid feed stream comprising 1,4-butanediol and a minor amount of 2-(4-hydroxybutoxy)-tetrahydrofuran and/or precursors thereof comprising
    passing the crude liquid feed in the presence of hydrogen in a reaction zone over a heterogeneous liquid tolerant copper catalyst in the liquid phase at hydrogenation conditions; and
    recovering a purified stream of 1,4-butanediol having a lower amount of 2-(4-hydroxybutoxy)-tetrahydrofuran than the crude liquid feed stream, wherein the crude liquid feed is a product stream from production of 1,4-butanediol which has not been subjected to prior purification.

2. A process according to claim 1 wherein hydrogen pressure is in the range of about 5 barg to about 150 barg.

3. A process according to claim 2 wherein the hydrogen pressure is about 35 barg to about 100 barg.

4. A process according to claim 1 wherein a temperature of the reaction zone is in the range of from about 20° C. to about 150° C.

5. A process according to claim 1 wherein a temperature of the reaction zone is in the range of from about 50° C. to about 130° C.

6. A process according to claim 1 wherein a liquid hourly space velocity is in the range of from about 0.1 to about 10.

7. A process according to claim 1 wherein a liquid hourly space velocity is in the range of from about 0.2 to about 5.

8. A process according to claim 1 wherein additional hydrogen is added.

9. A process according to claim 8 wherein the additional hydrogen is added at a flow rate of about 1 to about 50 normal liters per hour.

10. A process according to claim 8 wherein the hydrogen is added at a flow rate of about 5 and about 30 normal liters per hour.

11. A process according to claim 1 wherein the liquid tolerant copper catalyst is a copper chromite catalyst, a copper alumina catalyst, a copper zinc catalyst or a copper silica catalyst.

12. A process according to claim 1 wherein the catalyst is carried out in the presence of a promoter.

13. A process according to claim 12 wherein the promoter is manganese or barium.

14. A process for the production of at least one C$_4$ compound selected from 1,4-butanediol, tetrahydrofuran and γ-butyrolactone comprising:
    (a) contacting a solution of a di-(C$_1$-C$_4$ alkyl) maleate with hydrogen in a hydrogenation zone under ester hydrogenation conditions in the presence of a heterogeneous ester hydrogenation catalyst to convert the di-(C$_1$-C$_4$ alkyl) maleate to the at least one C$_4$ compound and a minor amount of 2-(4-hydroxybutoxy)-tetrahydrofuran;
    (b) recovering from the hydrogenation zone a product stream containing the at least one C$_4$ compound and a minor amount of 2-(4-hydroxybutoxy)-tetrahydrofuran as a crude feed stream; and
    (c) without prior purification subjecting the crude feed stream to the process of claim 1.

* * * * *